(12) United States Patent
Stewart et al.

(10) Patent No.: US 6,337,181 B1
(45) Date of Patent: Jan. 8, 2002

(54) METHOD OF SPECIFYING VACCINE COMPONENTS FOR VIRAL QUASISPECIES

(76) Inventors: Jeffrey Joseph Stewart, 1 Club Rd., Chatham, NJ (US) 07928; Samuel Litwin; Perry Watts, both of 8328 Roberts Rd., Elkins Pk., PA (US) 19027

( * ) Notice: Subject to any disclaimer, the term of this patent is extended or adjusted under 35 U.S.C. 154(b) by 0 days.

(21) Appl. No.: 09/217,293

(22) Filed: Dec. 21, 1998

(51) Int. Cl.[7] ............ C12Q 1/70; C12N 15/00; A01N 43/04; C07K 1/00
(52) U.S. Cl. ............ 435/5; 435/320.1; 435/325; 435/455; 514/44; 530/351; 424/93.21; 424/206.1; 424/184.1
(58) Field of Search ............ 424/93.21, 206.1, 424/184.1; 536/24.1, 23.1, 24.3, 24.33; 435/6, 172.3, 91.32, 91.33; 514/44; 530/351

(56) References Cited

PUBLICATIONS

VanCott TC et al, "Preferential antibody recognition structurally distinct HIV–1 gp 120 molecules", Journal of Acquired Immune Deficiency Syndromes, Nov. 1994, 7(11), pp. 1103–1115.*

Struck, M., "Vaccine R&D success rates and development times", Nature Biotechnology, vol. 14, May 1996, pp. 591–593.*

Wang, Wei–Kung et al, "Pattern of gp 120 sequence divergence linked to a lack of clinical progression inhuman immunodeficiency virus type 1 infection", Proc. Natl. Acad. Sci USA, vol. 93, Jun. 1996, pp. 6693–6697.*

* cited by examiner

Primary Examiner—John S. Brusca
Assistant Examiner—Stephen Siu

(57) ABSTRACT

An algorithm for determining the viral antigenic protein variants to be used to construct vaccines designed to immunize against variable viral populations (quasispecies) is described. The method entails analyzing multiple nucleotide sequences of viral proteins and identifying those variants that provide selective advantage to the virus. Examples are given for influenza A hemagglutinin 3 and HIV-1 gp120.

16 Claims, 2 Drawing Sheets

Fig. 1: Influenza HA

```
........10........20........30........40........50........60........70........80........90
QKLPGNDNSTATLCLGHHAVPNGTLVKTITNDQIEVTNATELVQSSSTGRICDSPHRILDGKNCTLIDALLGDPHCDGFQNKEWDLFVER
                                                                                 EK

.......100.......110.......120.......130.......140.......150.......160.......170.......180
SKAYSNCYPYDVPDYASLRSLVASSGTLEFINEDFNWTGVAQDGKSYACKRGSVNSFFSRLNWLHKLEYKYPALNVTMPNNGKFDKLYIW
   F                          T  G      T s g  S      K         YES s            D
                                          N T
                                            e

.......190.......200.......210.......220.......230.......240.......250.......260.......270
GVHHPSTDSDQTSLYVRASGRVTVSTKRSQQTVIPNIGSRPWVRGLSSRISIYWTIVKPGDILLINSTGNLIAPRGYFKIRNGKSSIMRS
     i  RE  N   Q                  D  Y      Q                                   T
        k                                    i

.......280.......290.......300.......310.......320.......330.......340.......
DAPIGNCSSECITPNGSIPNDKPFQNVNRITYGACPRYVKQNTLKLATGMRNVPEKQTRGIFGAIAGFIENGWEGMV
     T N                    K
```

Fig. 2: HIV gp120

```
                                                             β1
                                                            |-|      |
..........50........60........70........80........90......100
YGVPVWKEATTTLFCASDAKAYDTEVHNVWATHACVPTDPNPQEIVLENVTENFNMWKNNM
    rD k         rSHkA A  i              s   Ve G     k    E D
     d            s   k                      mh
     n                                       k
                                              p

α1           β2                 LV1/V2
  <-------------|  |---|
  .......110.......120.......130..    ......160.......170.....
  VEQMHEDIISLWDQSLKPCVKLTPLCVTLNCT {1} GEIKNCSFNITTSIRDKVQKEYAL
    d   QQ  V       sm          S      EgM    kVS NLKN MKRVH f
    n                                                eM      k
                                                     d       r
                                                             i

β3           β4        β5      LA
                   |-|       |------|  |------|
  ..180.....    190.......200.......210.......220.......230....
  FYKLDVVPID {2} TSYRLISCNTSVITQACPKVSFEPIPIHYCAPAGFAILKCNDKKFN
    RP  IIQ E     r  m TN  N Al    IT         T    Y V    N  S
                      h

β6   β7   β8     LB    β9   Lc  β10   LD     β11    β12
  |-|  |---||----|       |-|       |-|          |---|  |-->
  ...240.......250.......260.......270.......280.......290.....
  GTGPCTNVSTVQCTHGIRPVVSTQLLLNGSLAEEEVVIRSENFTDNAKTIIVQLNESVEIN
   K k Kp   S         K              GgII     INTI    kKP K T
   s T  r                              m         n    tt  t
        n                                         v

LV3           β13    α2               LE
  <|                        |---||------------|
  ..300.........*........-......330.......340.......350.......
  CTRPNNNTRKSIHIGPGRAFYATGDIIGDIRQAHCNISRAKWNNTLKQIVKKLREQFG-NK
    i    s       RGVPM    qT FTA-E  T N  K Y    LNKTE DKa QKVATQ  KKH kn
         g       t        KV -  q                GEd   e  g   tg  gr  -
                 s           r                   eka   r      a   q   E
                             k                         d          p
                                                                  n β14    β15 α3    β16    β17   α4  β18 LV4   β19    β20
  |---|   |-||---||---|   |----|  |--| |-|     <------||---|    |
  .-........370.......380.......390.....   ....420.......430
  T-IVFNQSSGGDPEIVMHSFNCGGEFFYCNTTQLFNSTW {3} ITLPCRIKQIINMWQEV
    It  I KPP-     L  tt       R      SSK  I-    I Q    FV L  K
         t an                          g
         n qs β21  LF    β22    β23    LV5   β24    α5     β25
  <---|    |-----||-------|     <----|  |--------||-----|
  .......440.......450..........  ..470.......480.......490..
  GKAMYAPPIRGQIRCSSNITGLLLTRDGG {4} ETFRPGGGDMRDNWRSELYKYKVVKIE
    Q     S E S v     I             I      N K           RVk
          k n k L                   v                    e
          e i   T
          q .....500.......510.
  PLGVAPTKAKRRVVQREKR
    i I     R    e
              a   g
```

US 6,337,181 B1

METHOD OF SPECIFYING VACCINE COMPONENTS FOR VIRAL QUASISPECIES

INTRODUCTION

This invention was made in the course of research sponsored by the National Institutes of Health. The U.S. Government may have certain rights in this invention.

BACKGROUND OF THE INVENTION

Many RNA viruses do not have a single, representative genome but instead form a "quasispecies"—a set of related viral variants that coexist in field populations and even within single infected individuals (reviewed in Holland, et al. 1992 Curr Top Microbiol Immunol 176:1–20, Smith, et al. 1997 J Gen Virol 78:1511–1519, Domingo, et al. 1985 Gene 40:1-8, Domingo, et al. 1995 Molecular Basis of Virus Evolution 181–191, Duarte, et al. 1994 Infect Agents Dis 3:201–214). The emergence of immunologically distinct members of a viral quasispecies through mutation and subsequent immune selection is called "antigenic drift." Antigenic drift is thought to be important in HIV infection and the continuing seasonal influenza epidemics,especially because immunity generated against one viral variant rapidly selects for escape variants. Attributed to antigenic drift are the moderately high failure rate and the short-lived efficacy of influenza vaccines (Wilson and Cox 1990 Annu Rev Immunol 8:737–771), the failure of synthetic foot-and-mouth disease virus vaccines (Taboga, et al. 1997 J Virol 71:2606–2614), and the current failure of recombinant HIV vaccines to provide complete protection against field strains of the virus (Berman, et al. 1997 J Inf Dis 176:384–397).

If vaccination against a viral quasispecies is to be effective, either ubiquitous, unvarying viral targets must be identified or, alternately, all advantageous viral variants of one or more antigenic regions must be identified and included in a vaccine.

SUMMARY OF THE INVENTION

An object of the present invention is to provide a method of determining the advantageous variants found in a viral population given aligned nucleotide sequences of antigenic proteins or protein regions of that viral population. Once these advantageous variants are identified, they may be used drug targeting and in vaccine design applications.

The algorithm used to identify the advantageous variants is as follows for each amino acid position: 1) Identified as an advantageous variant of the viral population is the most common (consensus) amino acid. 2) Replacement variants, those viral variants that differ in the amino acid sequence from the consensus, that are found to have significantly high replacement to silent mutation ratios are determined to be advantageous to the virus. 3) Conversely, replacement variants with significantly low replacement to silent mutation ratios are recognized as providing selective disadvantage to the virus and so are excluded from further consideration. 4) Replacement variants where the nucleotide replacement to silent mutation ratio is unable to classify the variant as significantly advantageous or disadvantageous are provisionally identified as advantageous variants; the selective advantage or disadvantage of these variants cannot be determined with the given sequence data set, so advantage or disadvantage must be determined experimentally. A reasonable subset of variants may be selected by including the $2^{H+\sigma}$ most common variants (where H is the Shannon information content and $\sigma$ is its standard error of its estimation).

The identified advantageous viral variants may then be used for purposes including but not limited to: 1) specifying components of vaccines to be used in conjunction with appropriate vaccination vectors and techniques know in the art; 2) identifying appropriate targets for small molecule or other anti-viral compounds; 3) using constructed viral variant panels to screen for broadly neutralizing monoclonal antibodies, screen for broadly neutralizing anti-viral compounds, and/or determine the neutralization spectrum of anti-viral compounds or antibodies.

Examples are given for influenza A hemagglutinin 3 (SEQ ID NO: 1) and HIV-1 gp120. (SEQ ID NO: 2–SEQ ID NO: 6).

BRIEF DESCRIPTIONS OF THE FIGURES

FIG. 1 (SEQ ID NO: 1) depicts the advantageous variants of human-infecting influenza A hemagglutinin (H3 serotype). All variants identified as advantageous are presented in uppercase letters, where the letters refer to the standard amino acid abbreviations. Variants in lowercase letters are provisionally included as advantageous. Disadvantageous variants are not shown. The traditional antigenic sites, A (SEQ ID NO: 7), B (SEQ ID NO: 8), C, and D (SEQ ID NO: 9), are also indicated (Wiley, et al. 1981 Nature 289:373–378).

FIG. 2 (SEQ ID NO: 2–SEQ ID NO: 6) depicts the advantageous variants of human-infecting HIV-1 gp120, where the letters refer to the standard amino acid abbreviations; secondary structure identifiers are included for positional reference (Kwong, et al. 1998 Nature 393:648–659). Four regions (designated 1–4) were not reasonably alignable so are not included in the analysis. Variants identified as advantageous are presented in uppercase letters. Variants in lowercase letters are provisionally included as advantageous. Disadvantageous variants are not shown.

DETAILED DESCRIPTION OF THE INVENTION

Given that many viruses do not have a single, representative genome but instead form a "quasispecies"—a set of related viral variants—we decide which viral variants are advantageous to the viral population with the following algorithm (disadvantageous viral variants are "noise" and should be ignored):

The consensus (most common, mode) amino acid at each position is obviously advantageous, or it would not be the most common. Therefore, we identify the consensus amino acid at each viral position as advantageous.

We determine the non-consensus variants that provide advantage through replacement to silent mutation analysis. The replacement to silent mutation ratio (R:S) of each protein position is measured in order to identify variants that are advantageous. R:S is the number of nucleotide mutations that code for amino acid replacements divided by the number that code for the original amino acid. [To avoid division by zero, R/(R+S) is measured instead of R/S when there are no silent mutations at a protein position.] An observed high R:S indicates that the particular replacement variant is advantageous. Conversely, a low R:S indicates that the replacement variant is disadvantageous.

We determine the advantageous viral variants by measuring the R:S of each possible replacement mutation and then comparing this observed ratio to that which would be expected if antigenic drift were neutral. Critically, we do not test the overall R:S of the protein as an aggregate, nor do we test the R:S of a codon to all its replacement mutations taken as a whole. Rather, the large number of viral sequences at our disposal allows us to test the R:S of each particular replacement. That is, we measure the R:S of the mutations from a consensus codon towards each individual amino acid. For example, if the consensus codon were ttt (Phe), we would test the R:Ss of all point mutations from ttt. One of these mutations is ttt→tat (Tyr). We calculate the expected R:S for ttt→tat under the null hypothesis of neutral drift. The expected S is one because only one mutation (ttc) is silent, and the expected R is also one because only one point mutation of ttt (tat) codes for Tyr, so the expected R:S is one, in this case. This R:S is then compared to the observed R:S to determine if the null hypothesis may be rejected. If neutral drift is rejected and the observed R:S is high, then this replacement is determined to confer selective advantage on the virus. Conversely, if the null hypothesis is rejected and R:S is lower than expected under the neutral drift hypothesis, then the replacement is determined to confer selective disadvantage on the virus. The procedure is repeated for all other point mutations.

We use R:S to reject the null hypothesis that the mutational space surrounding the most common codon is randomly distributed among all nine possible R or S nucleotide point mutations. In rejecting this null hypothesis, the actual ancestral sequences need not be determined. This allows R:S calculations to be applied to viral sequences whose ancestral sequence is unclear or unknown.

Empirical R:S is compared to neutral R:S by means of a two-sided test. For each codon, we test the null hypothesis that all nine single point mutations are equally probable. The quotient $p=R/(R+S)$ is the probability of a replacement mutation at this position if each nucleotide position is equally mutable and each of the three mutational targets at that codon are equally likely. The numerator, R, is the number of point mutations that lead from the consensus codon to the target amino acid (which can be greater than one under the hypothesis that each nucleotide position is equally mutable). Under this assumption, the chance of observing r replacement variants is given by the binomial distribution, $$b(r, n, p) = \binom{n}{r} p^r (1-p)^{(n-r)}$$

where n is the number of sequences providing data for this position. To form a two-sided test, we sum all terms b(k,n,p) such that b(k,n,p) is not greater than b(r,n,p), where k is in the set (0, . . . , n) and r is the number of observed replacement variants. We reject the null hypothesis at the 100α% level of significance for a given α>0. In other words, we sum the chances of all events that are no more likely than that of the observation. If this sum is small (e.g., not greater than 0.05), we reject the null hypothesis (at the 5% level of significance in this example).

Advantageous Variant Notation

We present our results in the following format for each protein position:

1. The most common (consensus) amino acids are written in capital letters.

2. Beneath each consensus amino acid are written, in descending order of frequency, all non-consensus advantageous variants (also in capital letters).

3. Variants determined to be disadvantageous are excluded.

4. Interspersed among the advantageous variants according to their frequencies are variants where the neutral drift null hypothesis is not rejected. As a reasonable but arbitrary cut-off, we include the first $2^{H+\sigma}$ of the variants, where H is the Shannon information content of the site and where σ is its standard error of its estimation.

$$H = -\sum_{i=1}^{21} p_i \log_2 p_i,$$

where $p_i$ is the with fraction of amino acids at the site (the alignment gap is counted as a 21st amino acid) (Shannon 1949, Litwin and Jores 1992 Theoretical and experimental insights into immunology H 66:). Alignment gaps are considered distinct from data absences (which are artifacts of sequence fragmentation or indeterminate sequences); such data absences are excluded from calculation.

Applications of Advantageous Variants

The identified advantageous viral variants may then be used in applications including but not limited to: 1) specifying components of vaccines to be used in conjunction with appropriate vaccination vectors. 2) Identifying appropriate targets for small molecule and other anti-viral compounds. Given that particular viral protein targets are proposed based on a particular member of a viral population (e.g., by using a crystal structure of a particular protein), one may computationally and/or mathematically model the variants identified as advantageous to predict if the rms and other deviations from the known protein structure will either allow or disallow the effective use of the anti-viral compound with other advantageous variants of the viral quasispecies. 3) Using constructed viral variant panels to screen for broadly neutralizing monoclonal antibodies, screen for broadly neutralizing anti-viral compounds, or determine the neutralization spectra of such anti-viral compounds or antibodies.

Data Subdivision

In many cases it will be impractical to manufacture a vaccine that includes all advantageous variants identified for a full-length protein. Instead, one should select a subregion or subregions of the target protein. These subregions should be chosen as sites that are both immunogenic and spatially divided from other variable regions so that advantageous variants outside the selected region do not interfere with antibody binding. The "antigenic sites" (SEQ ID NO: 7–ID NO:9) defined by antibody competition are examples of appropriate subdivisions of the viral proteins (Wiley, et al. 1981 Nature 289:373–378).

One may also subdivide the sequence data so that appropriate advantageous variants are identified for a subset of the viral population. For instance, one may use the method to prepare a vaccine for the set of viral variants found in a particular geographical region, recently isolated viral variants, or the viral variants infecting a high-risk host population. The following non-limiting examples are provided to illustrate further the present invention.

EXAMPLES

Example 1

Influenza A Hemagglutinin 3

The hemagglutinin (HA) envelope surface glycoprotein, the major neutralizing determinant of influenza A, is a classic example of an antigenically-drifting protein (Webster, et al. 1982 Nature 296:115–121). HA's trimeric three-dimensional structure has been solved, and the Ab binding sites on HA have been demonstrated in HA/Ab co-crystals (Wiley, et al. 1981 Nature 289:373–378, Wilson, et al. 1981 Nature 289:366–373, Bizebard, et al. 1995 Nature 376:92–94). Walter Gerhard and colleagues demonstrated that monoclonal immune pressure leads to the selection of HA escape variants in model systems (Yewdell, et al. 1986 J Virol 57:623–628, Gerhard, et al. 1981 Nature 290:713–717). Later, Dimmock and colleagues showed that polyclonal anti-sera can also select for escape variants (Lambkin, et al. 1994 J Gen Virol 75:3493–3502, Cleveland, et al. 1997 Epidemiol Infect 118:149–154).

Given that HA has been identified as an appropriate subject for our algorithm, we analyzed 310 human-infecting HA isolates of the H3 serotype. Sequences were accessed from the public NIH GenBank database (http://www.ncbi.nlm.nih.gov/genbank/), pre-aligned with PILEUP (Wisconsin Package, Genetics Computer Group), then hand-aligned. The advantageous variants are shown in FIG. 1(SEQ ID NO: 1). All variants identified as advantageous are presented in uppercase letters, where the letters refer to the standard amino acid abbreviations. Variants in lowercase letters are provisionally included as advantageous. To make a vaccine, combinations of the identified advantageous variants are included in appropriate vaccine vectors. Of course, the variants should be confined to one or more experimentally determined regions where antibody binding is effective and where variants within the region abrogate antibody binding. For influenza A, these regions have been identified as antigenic sites A (SEQ ID NO: 7), B (SEQ ID NO: 8), C, and D (SEQ ID NO:9) (Wiley, et al. 1981 Nature 289:373–378) (FIG. 1). Thus, if one were to vaccinate against all advantageous antigenic site D variants, the following four sequences should be included in a vaccine: SGRVTVSTKRSQQTVIPNIGS, SGRVTVSTKRSQQTVIPDIGS, SGRVTVSTKRSQQTVIPNIGY, and SGRVTVSTKRSQQTVIPDIGY(SEQ ID NO: 9).

Example 2

HIV-1 gp120

The principle neutralizing determinant of HIV-1 lies on the gp120 protein and is subject to antigenic drift (Putney, et al. 1986 Science 234:1392–1395, Goudsmit, et al. 1988 Proc Natl Acad Sci U S A 85:4478–4482, Javaherian, et al. 1989 Proc Natl Acad Sci U S A 86:6768–6772, Nowak, et al. 1991 Science 254:963–969). That the immune response selects antigenic drift variants in HIV, in vivo, is inferred from patients where strong immune responses generally correlate with greater viral diversity (Wolinsky, et al. 1996 Science 272:537–542, Delwart, et al. 1997 J Virol 71:7498–7508, Lukashov, et al. 1995 J Virol 69:6911–6916, Liu, et al. 1997 J Virol 71:4284–4295, Ganeshan, et al. 1997 J Virol 71:663–677).

Given that gp120 has been identified as an appropriate subject for our algorithm, we analyzed 6,151 gp120 sequences from human HIV-1 field infections. Sequences were accessed from the public NIH GenBank database (http://www.ncbi.nlm.nih.gov/genbank/) and pre-aligned with PILEUP (Genetics Computer Group, Wisconsin Package 1997) and/or DIALIGN2 (Morgenstern, et al. 1998 Bioinformatics 14: 290–294) then hand-aligned. The advantageous variants are shown in FIG. 2 (SEQ ID NO:2–SEQ ID NO:6), where the letters refer to the standard amino acid abbreviations; structural identifiers are included for positional reference (Kwong, et al. 1998 Nature 393:648–659). Four regions (designated 1–4) were not reasonably alignable and so are not included in the analysis. As in FIG. 1, variants identified as advantageous are presented in uppercase letters. Variants in lowercase letters are provisionally included as advantageous. To make a vaccine, the combinations of the identified advantageous variants are included in appropriate vaccine vectors. Again, the variants in such a vaccine probably should be confined to one or more regions where antibody binding is effective and where variation within the region abrogates antibody binding. Two epitopes that may be appropriate regions of gp120 are the CD4-binding site epitope and CD4-induced epitope (Wyatt, et al. 1998 Nature 393:705–711).

What is claimed is:

1. A method of determining which naturally occurring amino acid variants of a protein, protein subregion, or antigenic site of a virus are selectively advantageous to said virus, said method comprising the following steps:

aligning multiple nucleotide sequences of said protein subregion, or antigenic site to each other (multiple sequence alignment);

for each aligned amino acid position (nucleotide codon), identifying as selectively advantageous to said virus the consensus (most common, mode) amino acid;

for each aligned amino acid position (nucleotide codon), determining the replacement to silent ratio of each amino acid replacement mutation (observed R:S);

for each aligned amino acid position (nucleotide codon), determining the replacement to silent ratio that would be expected if nucleotide mutation were neutral (expected R:S);

for each aligned amino acid position (nucleotide codon), comparing said observed R:S to said expected R:S by means of a statistical test;

for each aligned amino acid position (nucleotide codon), identifying as selectively advantageous to said virus non-consensus amino acid replacement variants that are determined by said statistical test to have a said observed R:S significantly higher than said expected R:S;

whereby identifying which naturally occurring amino acid variants of said viral protein, protein subregion, or antigenic site are selectively advantageous to said virus.

2. A method of claim 1 wherein said statistical test is a two-sided test of the binomial distribution and the level of said significance is 5%.

3. A method of claim 1 wherein said statistical test is a two-sided test of the binomial distribution and the level of said significance is 1%.

4. A method of claim 1 further comprising the following step for each said amino acid position (nucleotide codon):

provisionally identifying as selectively advantageous to said virus non-consensus amino acid replacement variants where said statistical test is unable to classify said observed R:S as significantly lower or significantly higher than said expected R:S.

5. A method of claim 1 further comprising the following step for each said amino acid position (nucleotide codon):

provisionally identifying as selectively advantageous to said virus said non-consensus amino acid replacement variants where said statistical test is unable to classify said observed R:S as significantly lower or significantly higher than said expected R:S and where said variants are observed or known to be in the $2^{H+\sigma}$ most common amino acid variants, where H is the Shannon information content and $\sigma$ is its standard error of estimation.

6. A method of claim 5 wherein said statistical test is a two-sided test of the binomial distribution and the level of said significance is 5%.

7. A method of claim 6 wherein said aligned nucleotide sequences comprise sequences of human-infecting influenza A H3 hemagglutinin and wherein identified selectively advantageous amino acid variants are SEQ ID NO: 1.

8. A method of claim 7 wherein said antigenic site is antigenic site A and wherein identified selectively advantageous amino acid variants are SEQ ID NO: 7.

9. A method of claim 7 wherein said antigenic site is antigenic site B and wherein identified selectively advantageous amino acid variants are SEQ ID NO: 8.

10. A method of claim 7 wherein said antigenic site is antigenic site D and wherein identified selectively advantageous amino acid variants are SEQ ID NO: 9.

11. A method of claim 6 wherein said aligned nucleotide sequences comprise sequences of human-infecting HIV-1 gp120 and wherein identified selectively advantageous amino acid variants are SEQ ID NO: 2 covalently bonded to SEQ ID NO: 3 covalently bonded to SEQ ID NO: 4 covalently bonded to SEQ ID NO: 5 covalently bonded to SEQ ID NO: 6.

12. A method of identifying appropriate small molecule or other anti-viral compounds, said method comprising the following steps given a viral protein structure:

identifying selectively advantageous amino acid variants by any one of the methods claimed in claims 1–11;

modeling said variants computationally or mathematically to predict if rms and other deviations from known or observed protein structure will either allow or disallow effective use of said anti-viral compound, the preferred embodiment of said prediction comprising a prediction of binding.

13. A method of screening for broadly neutralizing monoclonal antibodies, said method comprising the following steps:

identifying, according to the method of claim 1, selectively advantageous amino acid variants;

constructing a panel of proteins, peptides, or viruses comprising said variants;

screening said antibodies for broad reactivity, the preferred embodiment of said screening comprising a binding assay.

14. A method of screening for broadly neutralizing antiviral compounds, said method further comprising the following steps:

identifying, according to the method of claim 1, selectively advantageous amino acid variants;

constructing a panel of proteins, peptides, or viruses comprising said variants;

screening said compounds for broad reactivity, the preferred embodiment of said screening comprising a binding assay.

15. A method of claim 1 further comprising the following step: subdividing said sequence data so that selectively advantageous amino acid viral variants are identified for a subset of said nucleotide sequences.

16. A method of claim 15 wherein said subset of said nucleotide sequences is selected from the group comprising said nucleotide sequences known or observed to be: in a particular geographical region, recently isolated, and infecting a high-risk host population.

* * * * *

SEQUENCE LISTING

```
<160> NUMBER OF SEQ ID NOS:  9

<210> SEQ ID NO 1
<211> LENGTH: 347
<212> TYPE: PRT
<213> ORGANISM: Influenza A virus
<220> FEATURE:
<223> OTHER INFORMATION: Xaa1 is KE; Xaa2 is EK; Xaa3 is YF; Xaa4 is
      IT; Xaa5 is DG; Xaa6 is AT; Xaa7 is DsN; Xaa8 is KgTe;
      Xaa9 is AS; Xaa10 is NK
<223> OTHER INFORMATION: Xaa11 is HY; Xaa12 is KE; Xaa13 is LS; Xaa14
      is Ys; Xaa15 is GD; Xaa16 is Si; Xaa17 is SRk; Xaa18
      is DE; Xaa19 is SN; Xaa20 is RQ
<223> OTHER INFORMATION: Xaa21 is ND; Xaa22 is SY; Xaa23 is LQi; Xaa24
      is NT; Xaa25 is NT; Xaa26 is SN; Xaa27 is RK
<223> OTHER INFORMATION: Capital letters indicate advantageous variants
      and lowercase letters indicate possibly advantageous
      variants (see detailed description)

<400> SEQUENCE: 1

Gln Lys Leu Pro Gly Asn Asp Asn Ser Thr Ala Thr Leu Cys Leu Gly
 1               5                  10                  15

His His Ala Val Pro Asn Gly Thr Leu Val Lys Thr Ile Thr Asn Asp
            20                  25                  30
```

-continued

```
Gln Ile Glu Val Thr Asn Ala Thr Glu Leu Val Gln Ser Ser Ser Thr
        35                  40                  45

Gly Arg Ile Cys Asp Ser Pro His Arg Ile Leu Asp Gly Lys Asn Cys
 50                  55                  60

Thr Leu Ile Asp Ala Leu Leu Gly Asp Pro His Cys Asp Gly Phe Gln
 65                  70                  75                  80

Asn Xaa Xaa Trp Asp Leu Phe Val Glu Arg Ser Lys Ala Xaa Ser Asn
                 85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Xaa Asn Glu Xaa Phe Asn Trp Thr
        115                 120                 125

Gly Val Xaa Gln Xaa Gly Xaa Ser Tyr Xaa Cys Lys Arg Gly Ser Val
130                 135                 140

Xaa Ser Phe Phe Ser Arg Leu Asn Trp Leu Xaa Xaa Xaa Glu Xaa Lys
145                 150                 155                 160

Tyr Pro Ala Leu Asn Val Thr Met Pro Asn Asn Xaa Lys Phe Asp Lys
                165                 170                 175

Leu Tyr Ile Trp Gly Val His His Pro Xaa Thr Asp Xaa Xaa Gln Thr
            180                 185                 190

Xaa Leu Tyr Val Xaa Ala Ser Gly Arg Val Thr Val Ser Thr Lys Arg
        195                 200                 205

Ser Gln Gln Thr Val Ile Pro Xaa Ile Gly Xaa Arg Pro Trp Val Arg
210                 215                 220

Gly Xaa Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Xaa Gly Lys Ser Ser Ile Met Arg Ser Asp Ala
            260                 265                 270

Pro Ile Gly Xaa Cys Xaa Ser Glu Cys Ile Thr Pro Asn Gly Ser Ile
        275                 280                 285

Pro Asn Asp Lys Pro Phe Gln Asn Val Asn Xaa Ile Thr Tyr Gly Ala
290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val
            340                 345
```

<210> SEQ ID NO 2
<211> LENGTH: 34
<212> TYPE: PRT
<213> ORGANISM: Human immunodeficiency virus type 1
<220> FEATURE:
<223> OTHER INFORMATION: Xaa1 is GE; Xaa2 is Eg; Xaa3 is IM; Xaa4 is Nk; Xaa5 is IV; Xaa6 is TS; Xaa7 is SNed; Xaa8 is ILM; Xaa9 is RK; Xaa10 is DN
<223> OTHER INFORMATION: Xaa11 is VMkri; Xaa12 is QK; Xaa13 is KR; Xaa14 is EV; Xaa15 is YH; Xaa16 is Lf; Xaa17 is KR; Xaa18 is LP; Xaa19 is VI; Xaa20 is VI
<223> OTHER INFORMATION: Xaa21 is PQ; Xaa22 is DE
<223> OTHER INFORMATION: Capital letters indicate advantageous variants and lowercase letters indicate possibly advantageous variants (see detailed description)

<400> SEQUENCE: 2

-continued

```
Xaa Xaa Xaa Lys Asn Cys Ser Phe Xaa Xaa Xaa Thr Xaa Xaa Xaa Xaa
 1               5                  10                  15

Lys Xaa Xaa Xaa Xaa Xaa Ala Xaa Phe Tyr Xaa Xaa Asp Xaa Xaa Xaa
             20                  25                  30

Ile Xaa
```

<210> SEQ ID NO 3
<211> LENGTH: 207
<212> TYPE: PRT
<213> ORGANISM: Human immunodeficiency virus type 1
<220> FEATURE:
<223> OTHER INFORMATION: Xaa1 is Tr; Xaa2 is Rm; Xaa3 is IT; Xaa4 is
      SNh; Xaa5 is TN; Xaa6 is VA; Xaa7 is Il; Xaa8 is VI;
      Xaa9 is ST; Xaa10 is AT
<223> OTHER INFORMATION: Xaa11 is FY; Xaa12 is IV; Xaa13 is DN; Xaa14 is
      NS; Xaa15 is TKs; Xaa16 is PkT; Xaa17 is TKrn;
      Xaa18 is Np; Xaa19 is TS; Xaa20 is RK
<223> OTHER INFORMATION: Xaa21 is EG; Xaa22 is Eg; Xaa23 is VI; Xaa24 is
      VIm; Xaa25 is FI; Xaa26 is DN; Xaa27 is AT; Xaa28
      is TInv; Xaa29 is Nk; Xaa30 is Ekt
<223> OTHER INFORMATION: Xaa31 is SPt; Xaa32 is EKt; Xaa33 is NT; Xaa34
      is Ti; Xaa35 is Nsg; Xaa36 is KR; Xaa37 is SG; Xaa38
      is IV; Xaa39 is HPts; Xaa40 is IM
<223> OTHER INFORMATION: Xaa41 is RqK; Xaa42 is AT; Xaa43 is YF; Xaa44
      is AT-; Xaa45 is TA; Xaa46 is G-; Xaa47 is DEqrk;
      Xaa48 is IT; Xaa49 is DN; Xaa50 is QK
<223> OTHER INFORMATION: Xaa51 is HY; Xaa52 is IL; Xaa53 is SN; Xaa54 is
      RKGe; Xaa55 is ATEk; Xaa56 is KEda; Xaa57 is ND;
      Xaa58 is NKer; Xaa59 is Ta; Xaa60 is KQg
<223> OTHER INFORMATION: Xaa61 is QK; Xaa62 is IV; Xaa63 is VAt; Xaa64
      is KTgad; Xaa65 is KQ; Xaa66 is RKgq; Xaa67 is EKr;
      Xaa68 is QH; Xaa69 is Gk-Epn; Xaa70 is -n; Xaa71
      is TI ; Xaa72 is -t
<223> OTHER INFORMATION: Xaa73  is Vitn Xaa74 is NKaq; Xaa75 is QPns;
      Xaa76 is SP; Xaa77 is S-; Xaa78 is PL; Xaa79 is VtI
<223> OTHER INFORMATION: Xaa80 is Mt; Xaa81 is GR; Xaa82 is TS; Xaa83 is
      TS; Xaa84 is QKg; Xaa85 is TI; Xaa86 is W-
<223> OTHER INFORMATION: Capital letters indicate advantageous variants
      and lowercase letters indicate possibly advantageous
      variants (see detailed description)

<400> SEQUENCE: 3

```
Xaa Ser Tyr Xaa Leu Xaa Xaa Cys Asn Xaa Ser Xaa Xaa Thr Gln Ala
 1               5                  10                  15

Cys Pro Lys Xaa Xaa Phe Glu Pro Ile Pro Ile His Tyr Cys Xaa Pro
             20                  25                  30

Ala Gly Xaa Ala Xaa Leu Lys Cys Asn Xaa Lys Lys Phe Xaa Gly Xaa
         35                  40                  45

Gly Xaa Cys Xaa Xaa Val Ser Xaa Val Gln Cys Thr His Gly Ile Xaa
     50                  55                  60

Pro Val Val Ser Thr Gln Leu Leu Leu Asn Gly Ser Leu Ala Glu Xaa
 65                  70                  75                  80

Xaa Xaa Xaa Ile Arg Ser Glu Asn Xaa Thr Xaa Asn Xaa Lys Xaa Ile
                 85                  90                  95

Ile Val Gln Leu Xaa Xaa Xaa Val Xaa Ile Xaa Cys Xaa Arg Pro Xaa
             100                 105                 110

Asn Asn Thr Arg Xaa Xaa Xaa Xaa Xaa Gly Pro Gly Xaa Xaa Phe Xaa
             115                 120                 125

Xaa Xaa Xaa Xaa Ile Xaa Gly Xaa Ile Arg Xaa Ala Xaa Cys Asn Xaa
         130                 135                 140

Xaa Xaa Xaa Xaa Trp Xaa Xaa Xaa Leu Xaa Xaa Xaa Xaa Xaa Xaa Leu
145                 150                 155                 160

Xaa Xaa Xaa Phe Xaa Xaa Asn Lys Xaa Xaa Ile Xaa Phe Xaa Xaa Xaa
             165                 170                 175
```

```
Xaa Gly Gly Asp Xaa Glu Ile Xaa Xaa His Ser Phe Asn Cys Xaa Gly
            180                 185                 190

Glu Phe Phe Tyr Cys Asn Xaa Xaa Xaa Leu Phe Asn Ser Xaa Xaa
        195                 200                 205

<210> SEQ ID NO 4
<211> LENGTH: 46
<212> TYPE: PRT
<213> ORGANISM: Human immunodeficiency virus type 1
<220> FEATURE:
<223> OTHER INFORMATION: Xaa1 is TI; Xaa2 is PQ; Xaa3 is IF; Xaa4 is IV;
      Xaa5 is Ml; Xaa6 is EK; Xaa7 is KQ; Xaa8 is RSkeq;
      Xaa9 is QEni; Xaa10 is RSk
<223> OTHER INFORMATION: Xaa11 is SvL; Xaa12 is LI
<223> OTHER INFORMATION: Capital letters indicate advantageous variants
      and lowercase letters indicate possibly advantageous
      variants (see detailed description)

<400> SEQUENCE: 4

Ile Xaa Leu Xaa Cys Arg Ile Lys Gln Xaa Xaa Asn Xaa Trp Gln Xaa
 1               5                  10                  15

Val Gly Xaa Ala Met Tyr Ala Pro Pro Ile Xaa Gly Xaa Ile Xaa Cys
            20                  25                  30

Xaa Ser Asn Ile Thr Gly Leu Xaa Leu Thr Arg Asp Gly Gly
         35                  40                  45

<210> SEQ ID NO 5
<211> LENGTH: 46
<212> TYPE: PRT
<213> ORGANISM: Human immunodeficiency virus type 1
<220> FEATURE:
<223> OTHER INFORMATION: Xaa1 is TIv; Xaa2 is DN; Xaa3 is RK; Xaa4 is
      KRe; Xaa5 is IV; Xaa6 is Ek; Xaa7 is Li; Xaa8 is VI;
      Xaa9 is KRa; Xaa10 is Qeg
<223> OTHER INFORMATION: Capital letters indicate advantageous variants
      and lowercase letters indicate possibly advantageous
      variants (see detailed description)

<400> SEQUENCE: 5

Glu Xaa Phe Arg Pro Gly Gly Gly Xaa Met Xaa Asp Asn Trp Arg Ser
 1               5                  10                  15

Glu Leu Tyr Lys Tyr Lys Val Val Xaa Xaa Xaa Pro Xaa Gly Xaa Ala
            20                  25                  30

Pro Thr Xaa Ala Lys Arg Arg Val Val Xaa Arg Glu Lys Arg
         35                  40                  45

<210> SEQ ID NO 6
<211> LENGTH: 93
<212> TYPE: PRT
<213> ORGANISM: Human immunodeficiency virus type 1
<220> FEATURE:
<223> OTHER INFORMATION: Xaa1 is Kr; Xaa2 is ED; Xaa3 is Tkdn; Xaa4 is
      Kr; Xaa5 is AS; Xaa6 is YH; Xaa7 is Dks
<223> OTHER INFORMATION: Xaa8 is TA; Xaa9 is VAk; Xaa10 is Vi; Xaa11 is
      Ns; Xaa12 is IVm; Xaa13 is Vehkp
<223> OTHER INFORMATION: Xaa14 is EG; Xaa15 is Nk; Xaa16 is KE; Xaa17 is
      ND; Xaa18 is Edn; Xaa19 is HQ
<223> OTHER INFORMATION: Xaa20 is EQ; Xaa21 is IV; Xaa22 is Ks; Xaa23 is
      Pm; Xaa24 is TS
<223> OTHER INFORMATION: Capital letters indicate advantageous variants
      and lowercase letters indicate possibly advantageous
      variants (see detailed description)

<400> SEQUENCE: 6

Tyr Gly Val Pro Val Trp Xaa Xaa Ala Xaa Thr Thr Leu Phe Cys Ala
 1               5                  10                  15
```

```
Ser Asp Ala Xaa Xaa Xaa Xaa Glu Xaa His Asn Xaa Trp Ala Thr
             20              25              30

His Ala Cys Val Pro Thr Asp Pro Xaa Pro Gln Glu Xaa Xaa Leu Xaa
         35              40              45

Asn Val Thr Glu Xaa Phe Asn Met Trp Xaa Asn Xaa Met Val Xaa Gln
     50              55              60

Met Xaa Xaa Asp Xaa Ile Ser Leu Trp Asp Ser Leu Xaa Xaa Cys
 65              70              75              80

Val Lys Leu Thr Pro Leu Cys Val Thr Leu Asn Cys Xaa
             85              90
```

<210> SEQ ID NO 7
<211> LENGTH: 25
<212> TYPE: PRT
<213> ORGANISM: Influenza A virus
<220> FEATURE:
<223> OTHER INFORMATION: Xaa1 is DG; Xaa2 is AT; Xaa3 is DsN; Xaa4 is
      KgTe; Xaa5 is AS; Xaa6 is NK
<223> OTHER INFORMATION: Capital letters indicate advantageous variants
      and lowercase letters indicate possibly advantageous
      variants (see detailed description)

<400> SEQUENCE: 7

```
Asn Glu Xaa Phe Asn Trp Thr Gly Val Xaa Gln Xaa Gly Xaa Ser Tyr
 1               5                  10                  15

Xaa Cys Lys Arg Gly Ser Val Xaa Ser
             20              25
```

<210> SEQ ID NO 8
<211> LENGTH: 43
<212> TYPE: PRT
<213> ORGANISM: Influenza A virus
<220> FEATURE:
<223> OTHER INFORMATION: Xaa1 is HY; Xaa2 is KE; Xaa3 is SRk; Xaa4 is
      DE; Xaa5 is SN
<223> OTHER INFORMATION: Capital letters indicate advantageous variants
      and lowercase letters indicate possibly advantageous
      variants (see detailed description)

<400> SEQUENCE: 8

```
Leu Xaa Xaa Leu Glu Tyr Lys Tyr Pro Ala Leu Asn Val Thr Met Pro
 1               5                  10                  15

Asn Asn Gly Lys Phe Asp Lys Leu Tyr Ile Trp Gly Val His His Pro
             20                  25                  30

Ser Thr Asp Xaa Xaa Gln Thr Xaa Leu Tyr Val
             35              40
```

<210> SEQ ID NO 9
<211> LENGTH: 21
<212> TYPE: PRT
<213> ORGANISM: Influenza A virus
<220> FEATURE:
<223> OTHER INFORMATION: Xaa1 is ND; Xaa2 is SY
<223> OTHER INFORMATION: Capital letters indicate advantageous variants
      and lowercase letters indicate possibly advantageous
      variants (see detailed description)

<400> SEQUENCE: 9

```
Gly Arg Val Thr Val Ser Thr Lys Arg Ser Gln Gln Thr Val Ile Pro
 1               5                  10                  15

Xaa Ile Gly Xaa Arg
             20
```